(12) United States Patent
Llop et al.

(10) Patent No.: US 10,398,530 B2
(45) Date of Patent: Sep. 3, 2019

(54) BONE FOUNDATION GUIDE SYSTEM AND METHOD

(71) Applicant: NATIONAL DENTEX, LLC, Palm Beach Gardens, FL (US)

(72) Inventors: Daniel R. Llop, Reno, NV (US); Armand C. Jusuf, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 510 days.

(21) Appl. No.: 14/921,111

(22) Filed: Oct. 23, 2015

(65) Prior Publication Data

US 2016/0038255 A1 Feb. 11, 2016

Related U.S. Application Data

(63) Continuation-in-part of application No. 14/214,555, filed on Mar. 14, 2014.
(Continued)

(51) Int. Cl.
 *A61C 8/00* (2006.01)
 *A61C 1/08* (2006.01)
 *A61C 8/02* (2006.01)

(52) U.S. Cl.
 CPC ............ *A61C 1/084* (2013.01); *A61C 8/0089* (2013.01); *A61C 8/0006* (2013.01)

(58) Field of Classification Search
 CPC ...... A61C 1/084; A61C 8/0089; A61C 8/0006
(Continued)

(56) References Cited

U.S. PATENT DOCUMENTS

| 5,018,970 A | 5/1991 | Stordahl |
| 5,725,376 A | 3/1998 | Poirier |

(Continued)

FOREIGN PATENT DOCUMENTS

| CA | 2795668 A1 | 11/2011 |
| CA | 2934371 A1 | 6/2015 |

(Continued)

OTHER PUBLICATIONS

Machine translation of PE 2425797 through https://worldwide.espacenet.com/?locale=en_EP, done on May 22, 2018.*
(Continued)

*Primary Examiner* — Heidi M Eide
*Assistant Examiner* — Mirayda A Aponte
(74) *Attorney, Agent, or Firm* — Frost Brown Todd LLC

(57) ABSTRACT

A bone foundation guide system and method, the system could includes a bone foundation guide including a body forming an open surgical space, the body further having a bottom contoured to reversibly affix to exposed bone of a dental surgical site and a top contoured to match a bottom side of a dental implant surgical guide; at least one anchoring strut that removably attaches to the body with an apex of the anchoring strut further denoting one or more indentations for matching up with and receiving one or more portions of one alveolar ridge that opposes another alveolar ridge supporting the dental surgical site; alternatively to the anchoring struts and a tissue spacing gasket, the dental implant surgical guide that removably connects to the body; and alternatively to the anchoring struts or the dental implant surgical guide, the tissue spacing gasket that removably connects to the body.

12 Claims, 14 Drawing Sheets

Related U.S. Application Data

(60) Provisional application No. 61/784,029, filed on Mar. 14, 2013.

(58) Field of Classification Search
USPC .................................................. 433/72
See application file for complete search history.

(56) References Cited

U.S. PATENT DOCUMENTS

| | | | |
|---|---|---|---|
| 5,967,777 A | 10/1999 | Klein et al. | |
| 6,319,006 B1 | 11/2001 | Scherer et al. | |
| 6,382,975 B1 | 5/2002 | Poirier | |
| 6,491,696 B1 | 12/2002 | Kunkel | |
| 6,672,870 B2 * | 1/2004 | Knapp | A61C 1/084 |
| | | | 433/75 |
| 6,814,575 B2 | 11/2004 | Poirier | |
| 6,997,707 B2 | 2/2006 | Germanier | |
| 7,331,786 B2 | 2/2008 | Poirier | |
| 7,632,097 B2 | 12/2009 | De Clerck | |
| 7,774,084 B2 | 8/2010 | Cinader, Jr. | |
| 7,824,181 B2 | 11/2010 | Sers | |
| 7,866,980 B2 | 1/2011 | Poirier | |
| 7,887,327 B2 | 2/2011 | Marotta | |
| 7,905,726 B2 | 3/2011 | Stumpel | |
| 7,909,606 B2 | 3/2011 | Marcello | |
| 7,942,668 B2 | 5/2011 | Brajnovic et al. | |
| 8,011,927 B2 | 9/2011 | Berckmans, III et al. | |
| 8,021,153 B2 | 9/2011 | Poirier | |
| 8,038,440 B2 | 10/2011 | Swaelens et al. | |
| 8,135,492 B2 | 3/2012 | Yau et al. | |
| 8,142,189 B2 * | 3/2012 | Brajnovic | A61B 17/176 |
| | | | 433/75 |
| 8,352,060 B2 | 1/2013 | Chun et al. | |
| 8,364,301 B2 | 1/2013 | Schmitt | |
| 8,371,849 B2 | 2/2013 | Gao | |
| 8,529,255 B2 | 9/2013 | Poirier et al. | |
| 8,540,510 B2 | 9/2013 | Brajnovic | |
| 8,574,302 B2 | 11/2013 | McKay | |
| 8,585,402 B2 | 11/2013 | Vogel et al. | |
| 8,706,672 B2 | 4/2014 | Malfliet et al. | |
| 8,770,972 B2 | 7/2014 | Swaelens et al. | |
| 8,777,612 B2 | 7/2014 | Suttin et al. | |
| 8,827,699 B2 | 9/2014 | Bavar | |
| 8,899,984 B2 | 12/2014 | Llop et al. | |
| 8,956,158 B2 * | 2/2015 | Schmalzle | A61C 1/082 |
| | | | 433/76 |
| 9,069,914 B2 | 6/2015 | Kopelman et al. | |
| 9,107,723 B2 | 8/2015 | Hall et al. | |
| 9,155,548 B2 | 10/2015 | Lin | |
| 9,155,599 B2 | 10/2015 | Thompson et al. | |
| 9,161,822 B2 | 10/2015 | Stevens et al. | |
| 9,168,112 B2 | 10/2015 | Haber | |
| 9,173,723 B2 | 11/2015 | Harrison | |
| 9,211,165 B2 | 12/2015 | Jamison | |
| 9,226,801 B2 | 1/2016 | Groscurth et al. | |
| 9,259,291 B2 | 2/2016 | Gantes | |
| 9,308,055 B2 | 4/2016 | Fisker et al. | |
| 9,336,336 B2 | 5/2016 | Deichmann et al. | |
| 9,358,082 B2 | 6/2016 | Nilsson | |
| 9,381,072 B2 | 7/2016 | Furrer et al. | |
| 9,402,698 B2 | 8/2016 | Thompson et al. | |
| 9,408,678 B2 | 8/2016 | Harrison | |
| 9,498,307 B2 | 11/2016 | Harrison | |
| 9,504,533 B2 | 11/2016 | Groscurth et al. | |
| 2006/0166169 A1 | 7/2006 | Dawood | |
| 2007/0162014 A1 | 7/2007 | Campbell et al. | |
| 2009/0092948 A1 | 4/2009 | Gantes | |
| 2009/0274990 A1 | 11/2009 | Kim | |
| 2009/0298008 A1 | 12/2009 | Groscurth et al. | |
| 2010/0035201 A1 | 2/2010 | Beck et al. | |
| 2010/0124731 A1 | 5/2010 | Groscurth et al. | |
| 2010/0316974 A1 | 12/2010 | Yau et al. | |
| 2011/0033819 A1 | 2/2011 | Freyer et al. | |
| 2011/0045431 A1 | 2/2011 | Groscurth et al. | |
| 2011/0045432 A1 | 2/2011 | Groscurth et al. | |
| 2011/0111371 A1 | 5/2011 | Haber | |
| 2011/0151399 A1 | 6/2011 | De Clerck et al. | |
| 2011/0256508 A1 | 10/2011 | Gantes | |
| 2012/0046914 A1 | 2/2012 | Gao | |
| 2012/0053593 A1 | 3/2012 | Abboud | |
| 2012/0156638 A1 | 6/2012 | Gantes | |
| 2012/0261848 A1 | 10/2012 | Haraszati | |
| 2012/0277899 A1 | 11/2012 | Chun et al. | |
| 2013/0011813 A1 | 1/2013 | Garcia et al. | |
| 2013/0023888 A1 | 1/2013 | Choi et al. | |
| 2013/0209956 A1 | 8/2013 | Sanders | |
| 2013/0252202 A1 | 9/2013 | Pardeller et al. | |
| 2014/0026419 A1 | 1/2014 | Haber | |
| 2014/0080086 A1 | 3/2014 | Chen | |
| 2014/0080092 A1 | 3/2014 | Suttin et al. | |
| 2014/0255873 A1 | 9/2014 | Bullis et al. | |
| 2014/0255876 A1 | 9/2014 | Alpern et al. | |
| 2014/0272778 A1 | 9/2014 | Llop | |
| 2014/0272779 A1 | 9/2014 | Okay | |
| 2014/0272780 A1 | 9/2014 | Llop | |
| 2015/0010881 A1 | 1/2015 | Llop | |
| 2015/0025855 A1 | 1/2015 | Fisker et al. | |
| 2015/0030995 A1 | 1/2015 | Villa | |
| 2015/0037756 A1 | 2/2015 | Berckmans, III et al. | |
| 2015/0093717 A1 | 4/2015 | Ali | |
| 2015/0111179 A1 | 4/2015 | Suttin | |
| 2015/0133956 A1 | 5/2015 | Dayan et al. | |
| 2015/0150684 A1 | 6/2015 | De Clerck | |
| 2015/0230894 A1 | 8/2015 | Juzbasic et al. | |
| 2015/0265372 A1 | 9/2015 | Kim et al. | |
| 2015/0272704 A1 | 10/2015 | Watson et al. | |
| 2015/0272705 A1 | 10/2015 | Watson et al. | |
| 2015/0302170 A1 | 10/2015 | Berckmans, III et al. | |
| 2015/0359614 A1 | 12/2015 | Sachdeva et al. | |
| 2015/0374460 A1 | 12/2015 | Sachdeva et al. | |
| 2016/0008110 A1 | 1/2016 | Harrison | |
| 2016/0038255 A1 | 2/2016 | Llop | |
| 2016/0106517 A1 | 4/2016 | Groscurth et al. | |
| 2016/0106518 A1 | 4/2016 | Choi et al. | |
| 2016/0128810 A1 | 5/2016 | Fostick et al. | |
| 2016/0157967 A1 | 6/2016 | Kim et al. | |
| 2016/0157970 A1 | 6/2016 | Gantes | |
| 2016/0278878 A1 | 9/2016 | Watson et al. | |
| 2016/0287336 A1 | 10/2016 | Kim et al. | |
| 2016/0324599 A1 | 11/2016 | Harrison | |
| 2016/0045280 A1 | 12/2016 | Haber | |
| 2017/0071697 A1 | 3/2017 | Groscurth et al. | |
| 2017/0112591 A1 | 4/2017 | Llop | |
| 2017/0112592 A1 | 4/2017 | Groscurth et al. | |
| 2017/0252126 A1 | 9/2017 | Llop | |

FOREIGN PATENT DOCUMENTS

| | | | |
|---|---|---|---|
| EP | 2 425 797 A1 | 3/2012 | |
| EP | 2425797 A1 * | 3/2012 | A61C 1/084 |
| MX | 2014001163 A | 7/2015 | |
| WO | WO 2010/061391 | 6/2010 | |
| WO | WO 2012/007615 | 1/2012 | |
| WO | WO 2014/130536 | 8/2014 | |
| WO | WO 2015/148891 | 10/2015 | |

OTHER PUBLICATIONS

International Search Report (PCT/USPTO Examining Authority) for PCT patent application entitled Bone Oundation Guide and Method of Use, applicant Daniel R. Llop, serial No. PCT/US2015/61002, filed Nov. 17, 2015.

Online Video of zygomatic dental implant surgery: http://www.youtube.com/watch?v=TGBXbP9aa2g&sns=em Title Zygomatic Implant Guided Surgery—Noris Medical, Published on Mar. 11, 2015, 1 pg.

Select pages showing a bone reduction guide from the publication Art of Computer Guided Implantology by Tradiev and Rosenfield, Copyright 2009, 3 pgs.

Website showing a bone reduction guide that was uploaded by www.dentalinformation.com on Aug. 4, 2011 located at https://

(56) References Cited

OTHER PUBLICATIONS www.youtube.com/watch?v=AZnReFZmLN8 the upload is entitled Bone Reduction and Bone Supported Guide for Dental Implant Surgery, 1 pg.
International Search Report and Written Opinion dated Mar. 2, 2016 for Application No. PCT/US2015/061002, 14 pgs.
International Search Report and Written Opinion dated Jul. 26, 2016 for Application No. PCT/US2016/021097, 13 pgs.
International Search Report and Written Opinion dated Jun. 16, 2017 for Application No. PCT/US2017/020746, 13 pgs.
International Search Report and Written Opinion dated Dec. 28, 2017 for Application No. PCT/US2017/054804, 10 pgs.

* cited by examiner

BONE FOUNDATION GUIDE SYSTEM AND METHOD

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention generally relates to dental implant and surgical guides. More particularity to those bone modification guides that incorporate a dental implant surgical guide.

BACKGROUND

As a person ages, they generally incur tooth and bone loss requiring prosthetic replacement as provided by the dental profession. One of the more important aspects of this replacement procedure is the need to solidly anchor within the available bone structure those implants used to secure individual (replacement artificial tooth) or collective (e.g., denture) dental prosthetic. When teeth lose bone around their roots, the bone (e.g., mandibular strut or the maxillary strut) may become uneven (either thinned out or too bulky) in various places in the respective dental strut. This bone condition may make the dental restorative process in that particular area more difficult than when such bone loss has not occurred. It could be thought as building a house whose foundation on an unleveled or uneven ground.

In order for the dental prosthetic (or restoration) to be properly fitted to the patient in a substantially esthetically and functionally acceptable position, the dental health care professional (e.g. dental surgeon) may first have to alter the bone of the dental surgical site (especially in those situations where the dental prosthetic is redressing significant tooth loss). This corrective process could start by making one or more incisions in gum area that otherwise designates the dental surgical or restoration site. These incisions substantially allow the gum tissue to be peeled back to expose the bone at the dental surgical site. The dental surgeon, in order to generally make dental surgical site/dental arch symmetrical in all relevant dimensions for the dental restoration (e.g., removable denture) or implant sites (e.g. fixed prosthetics) may then apply one or more cutting tools to generally reduce or remove unwanted high points or thickened places on the exposed bone structure. In other instances, the dental surgeon may add bone material to the exposed bone structure to further fill out the arch's profile or otherwise strengthen its structure.

During this process, the dental surgeon could bring the top portion of the alveolar ridge (e.g., one of the two jaw ridges either on the roof of the mouth or the bottom of the mouth that contain the sockets or alveoli of the teeth) to the correct surgical dimensions ("leveling out") by utilizing a bone foundation guide generally placed upon and secured to the bone structure to substantially guide the cutting/augmenting of the exposed bone. The bone foundation guide solves the problem of "estimating" the vertical height and width of the bone at the "coronal" level by guiding the surgeon's operation of the cutting tools and/or augmentation of the bone. This allows subsequent and accurate placement of the dental implants and respective prosthetics at the proper patient-specific vertical and horizontal levels. This bone adjustment process may also provide for the creation of the proper inter-occlusal room (e.g., the space that exists between the opposing teeth and the open tissue (e.g., that will receive the dental prosthetic) to generally insure that proper jaw operation and alignment, smile line and phonetics occur when the final dental prosthetic is finally located within the patient's mouth.

After the exposed bone has been properly been prepared (e.g., reduced or augmented), the bone foundation guide may be removed. A dental implant surgical guide may be subsequently fitted and attached in its place at the remodeled bone of dental surgical site. The dental implant surgical guide may be used to guide the operation of implant accessories needed to prepare the dental surgical site to receive the dental implants. The dental implant surgical guide may then be used to suitably locate the dental implants into the prepared bone structure. After the dental implants are properly located, the dental implant surgical guide may be removed and healing abutments (if required) may be fitted to the dental implants to create a space in the reattached gum proximate to the dental implant(s) that receives a portion (e.g., the base) of prosthetic or prosthesis (e.g., artificial tooth). Once the healing abutments are attached, the gum tissue may sutured back up and around the dental implant-healing abutment combination.

As needed, a full upper or full lower denture/tooth may be fitted to the implants either at the close of the dental surgery or later after healing of the tissues/osseo-integration of bone to implant(s) has occurred. Once the healing/osseo-integration has finalized, the dental surgeon could remove the healing abutments to open up the space proximate to the implants that receives the base of the prosthetic to place and affix the dental prosthetic securely to the implant(s).

The bone foundation guide and the implant dental surgical guide for the implants are generally considered separate instruments that are generally designed, manufactured and used independently of one another other. The design and creation of these guides can be now be accomplished through digital dentistry (e.g., pre-surgical digital methods and associated apparatuses to obtain and merge medical imaging information taken from the patient's mouth and/or dental castings of the patient's mouth to create a patient-specific virtual models of the preoperative and post-operative mouth and a surgical plan connecting the two models) or manually by dental art and hand (e.g., analogue dental design and preparation).

This separation or compartmentalization of dental guide capabilities could result in higher costs, manpower, and surgical time that could be found than if the two dental guides could be combined into one multipurpose device. The use of such a combination dental appliance could accordingly lead to an increase in the affordability of such dental procedures and results.

Another issue that may arise in such dental implant surgeries is when the dental healthcare professionals locate and affix the bone foundation guide physically upon the dental surgical site (e.g., a portion of bone.) Generally, the dental healthcare professional has to juggle both tasks of locating and affixing (e.g., drilling into the bone for fasteners, then using fasteners to secure the bone foundation guide onto bone) at the same time. The dental healthcare professional in having juggling both tasks may not properly locate the bone foundation guide in desired area of the dental surgical site; may not properly secure the bone foundation guide in place or both.

What could be needed is the present invention namely a bone foundation guide system substantially comprising of a combination of a bone foundation guide used to modify bone structure from a dental implant site (e.g., removing bone with a saw from the bone portion of the dental surgical site; adding bone or a bone analogue to the bone portion of the dental surgical site or both); a dental implant surgical guide (e.g., for generally locating implants to the dental surgical site) and alternatively to the dental implant surgical guide a tissue spacing gasket (e.g., for properly locating a prosthesis relative to the bone foundation guide.)

In one embodiment, a dental implant surgical guide be could removably attached to the bone foundation guide in situ (e.g., after the bone foundation guide has been used to modify a bone structure.) Substantially using the bone foundation guide as a base, the dental surgical implant guide could be used to generally position and locate the implant components (e.g., drill, reamers, abutments, implant drivers, etc.), dental implant or alike into the bone portion of the dental surgical site. Once the implant(s) are properly placed at the dental surgical site, the dental implant surgical guide could be removed from the bone foundation guide and be alternatively replaced with the tissue spacing gasket. In one possible embodiment, the tissue spacing gasket could be located between the bone foundation guide and a prosthesis to at least provide a basic approximation of gum tissue thickness for the gum that would normally cover that area of the dental surgical site to substantially allow for proper adjustment of prosthesis attachment to the implants and alike.

In one possible embodiment, the bone foundation guide could comprise of a body and one or more removable anchoring struts that reversibly connect buccal and lingual walls of the body, an apex of the anchoring strut could denote one or more indentations whose contours matching up with one or more portions of dentition, tissue or both from an opposing alveolar ridge (e.g., the alveolar ridge that is generally located opposite of the alveolar ridge that is hosting the dental implant site) to allow the indentions to removably receive the one or more portions of dentition, tissue or both from an opposing alveolar ridge. In this manner, the patient can then press the patient's at least the one or more portions of dentition, tissue or both of an opposing alveolar ridge upon at least one of the one or more the anchoring struts removably applied to the body to initially hold the bone foundation guide in place upon the dental surgical site. The patient's action could free the attending dental healthcare professional from having to hold the bone foundation guide in place and substantially allow the said professional to use both hands to secure the bone foundation guide in place with fasteners.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide an dental implant surgical guide that removably combines with a bone foundation guide to properly place a dental implant-retained prosthesis to a dental surgical site in a manner that reduces patient stress and bruising that may occur than if the two guides were applied separately;

the ability to use a digital virtual model of patent mouth to design a bone foundation guide wherein both the bone foundation guide and a dental implant surgical guide can be conjoined in situ properly locate a one or more dental implants that could be used to locate and secure a fixed dental prosthetic;

to provide a bone foundation guide and dental implant surgical guide that can be combined together to substantially reduce cost, time and man-hours needed in a dental implant surgical procedure to properly locate and attach a dental prosthetic to a dental surgical site;

the ability to use digital dentistry to control the design and manufacture of a dental implant surgical guide-bone foundation guide combination in a manner that digitally controls and refines the accuracy of the resulting bone foundation guide; dental implant surgical guide and a final fixed prosthetic; and to provide a bone foundation guide that is used in conjunction with a tissue spacing gasket, the tissue spacing gasket being used to help properly locate the placement of a prosthesis relative to the placed dental implant(s) by generally taking into account the height (or depth) of gum tissue that could normally cover the exposed bone at the dental implant surgical site;

the ability to design and manufacture a bone foundation guide system wherein a dental implant surgical guide or a tissue spacing gasket that could alternatively could mate and interlock with the bone foundation to generally allow implant components, dental implant or both to pass through the assembled combination onto the bone at a dental surgical guide;

to provide a dental surgical implant guide, bone foundation guide, and tissue spacing gasket to have matching contours and aligned openings and apertures that allow guides and gasket to be assembled into combinations to properly locate and attach a fixed prosthetic to an implant at a dental surgical site;

to provide one or more anchoring struts that could removably and temporarily attach to the front and back of the base of a bone foundation guide, each anchoring strut at a respective apex further define one or more indentations can reversibly receive one or more portions of the tissue, dentition or both of an alveolar ridge that is located opposite of an alveolar ridge that is supporting the dental surgical site;

the ability to have the patient bring one or more portions of the dentition, gum tissue or alike of an alveolar ridge into contact with the anchoring struts to hold the bone foundation guide in place upon the dental surgical site located on the opposing alveolar ridge;

to provide anchoring struts that can be removed from the bone foundation guide after the bone foundation guide has been secured to the dental surgical site by fasteners; and the ability to have the patient temporarily hold the bone foundation guide in place upon the dental surgical site so as to free the dental health care professional from holding the bone foundation guide in place and being able to concentrate instead on securing the bone foundation guide to the dental surgical site with one or more fasteners.

These and other advantages may be realized by reference to the remaining portions of the specification, claims, and abstract.

BRIEF DESCRIPTION OF ONE EMBODIMENT OF THE PRESENT INVENTION

One possible embodiment of the invention could be a bone foundation guide comprising a body having a buccal wall and a lingual wall that is continuously connected by a first end and a second end forming an open surgical space connecting a top of the body with a bottom of the body, the bottom is contoured to reversibly affix the body to at least a portion of a bone segment of a dental implant surgical site while the top is contoured to match a bottom side of a dental implant surgical guide as well as to guide the modification of a portion of the bone segment; one or more struts, at least one of the one or more struts removably attaches to body to connect the buccal wall to the lingual wall, the apex of the strut further denoting an one or more indentations for matching and receiving one or more portions of an opposing alveolar ridge; alternatively to the one or more anchoring struts or a tissue spacer gasket, the dental implant surgical guide that removably connects to the body; and alternatively to the one or more anchoring struts or dental implant surgical guide, a tissue spacing gasket that is removably attaches to the body.

Yet another embodiment of the invention could be a bone reduction guide comprising a body having a buccal wall and a lingual wall that is continuously connected by a first end and a second end forming an open surgical space connecting a top of the body with a bottom of the body, the bottom is contoured to reversibly affix to at least a portion of a bone segment of the bottom is contoured to reversibly affix to a bone segment of a dental implant surgical site while the top is contoured to guide at least an alteration of the bone segment of a dental surgical site; and one or more anchoring struts, at least one such anchoring strut having the apex denoting an one or more indentations having at least one contour that matches one or more portions of one alveolar ridge that is opposite of an alveolar ridge that supports the dental implant site, the at least one such anchoring struts removably attaches to the body.

Still another possible embodiment of the invention could be a method of holding a bone foundation guide in place at a dental surgical site comprising the following steps providing a bone foundation guide comprising a body having a buccal wall and a lingual wall that is continuously connected by a first end and a second end forming an open surgical space connecting a top of the body with a bottom of the body, the bottom is further contoured to removably receive at least a portion of a bone segment of a dental implant surgical site; providing at least one anchoring strut having an apex denoting one or more indentations for receiving one or more portions of a dentition, tissue or both of a first alveolar ridge that is opposing a second alveolar ridge supporting the dental surgical site; removably attaching at least at least one anchoring strut to the body; bringing at least one of the one or more portions into contact at least one anchoring strut; and holding the bone foundation guide in place upon the dental surgical site by bringing the first alveolar ridge into contact with the at least one anchoring strut.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
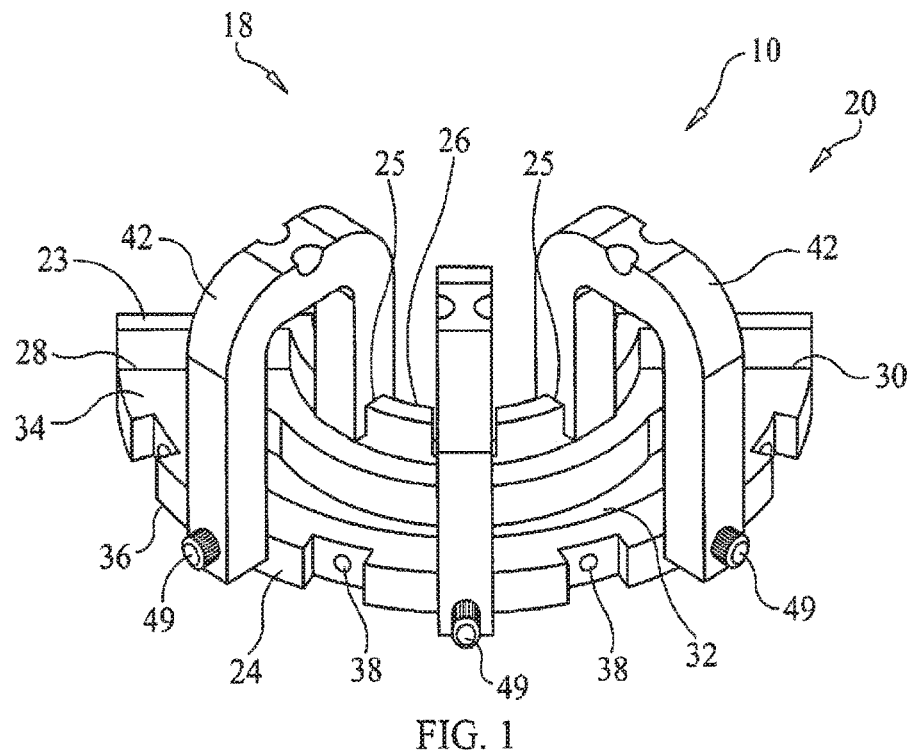
FIG. 1 is substantially a perspective bottom side view of one possible embodiment of the bone foundation guide the invention.
Figure 2:
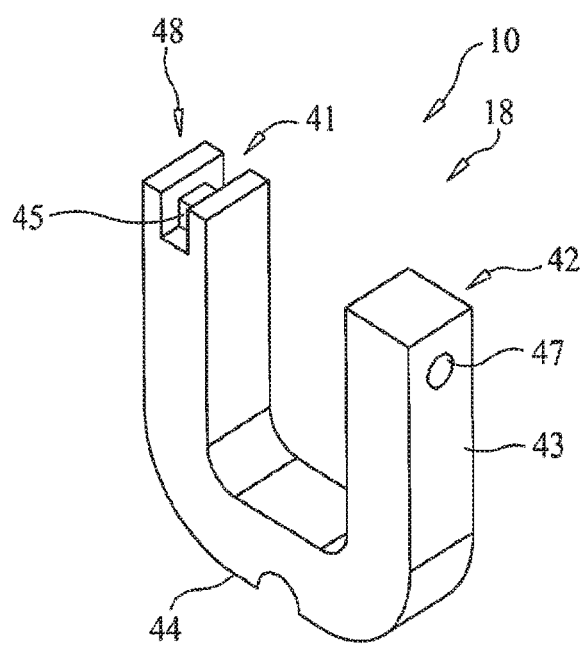
FIG. 2 is a top side perspective view of one possible embodiment of anchoring strut of the present invention.
Figure 3:
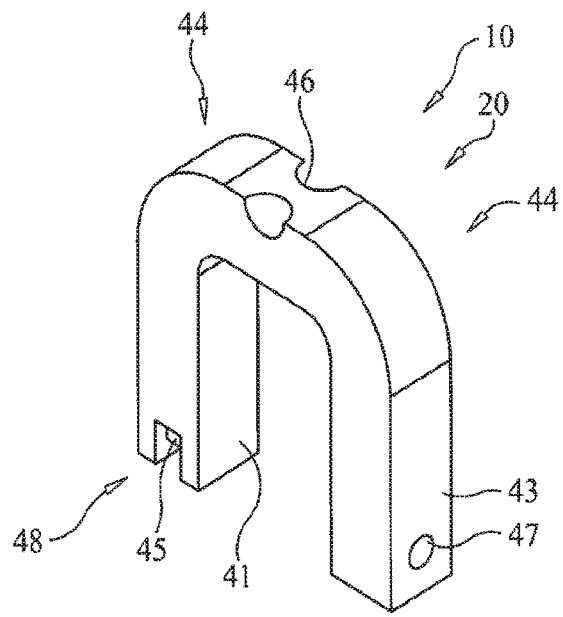
FIG. 3 is a bottom side perspective view of one possible embodiment of anchoring strut of the present invention.
Figure 4:
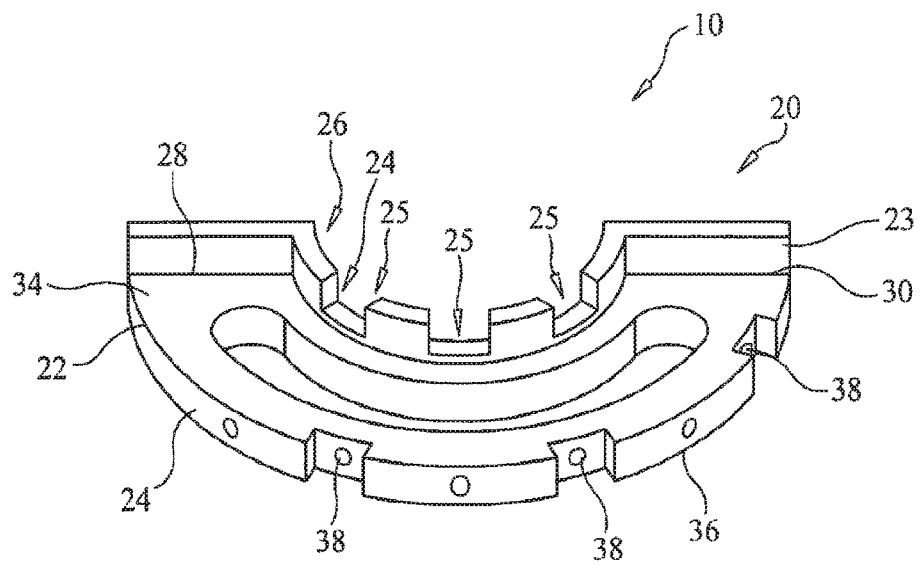
FIG. 4 is substantially a bottom side perspective view of one possible embodiment of the body.
Figure 5:
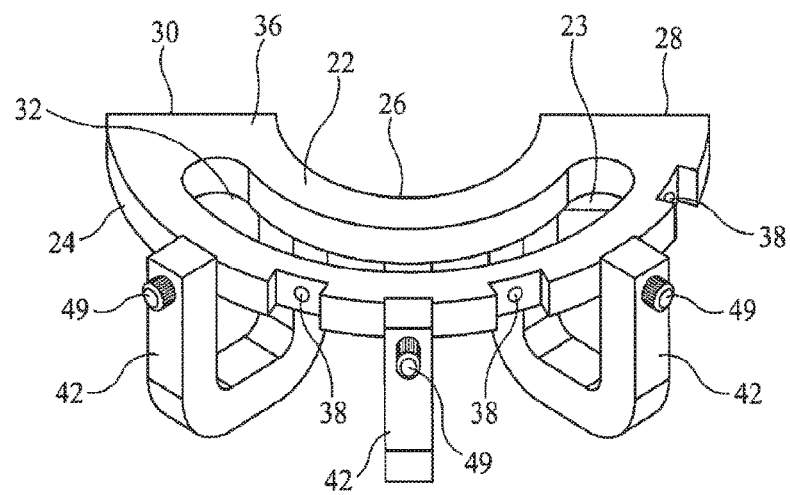
FIG. 5 is substantially a perspective top side view of one embodiment of the bone foundation guide.
Figure 6:
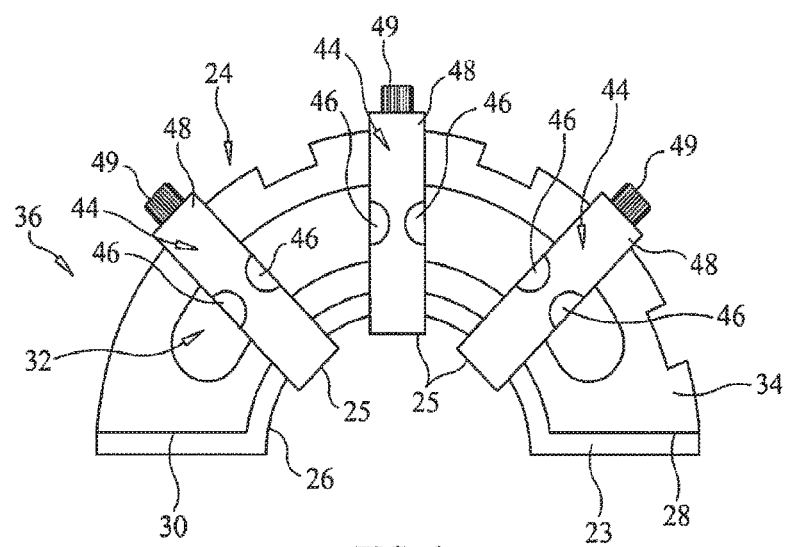
FIG. 6 is substantially a bottom elevation view of one embodiment of the bone foundation guide.
Figure 7:
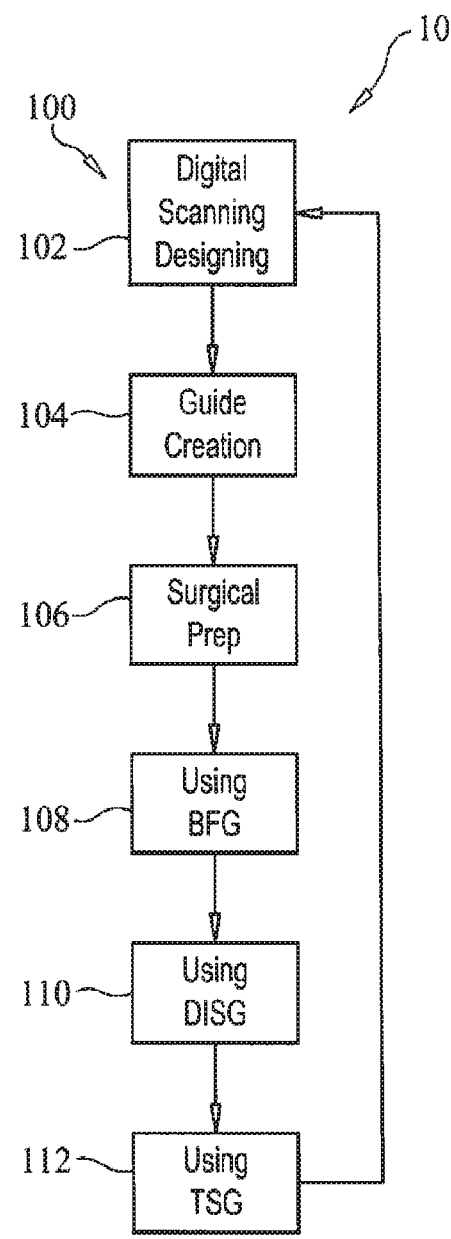
FIG. 7 is substantially a flow chart schematic showing a method of using the invention.
Figure 8:
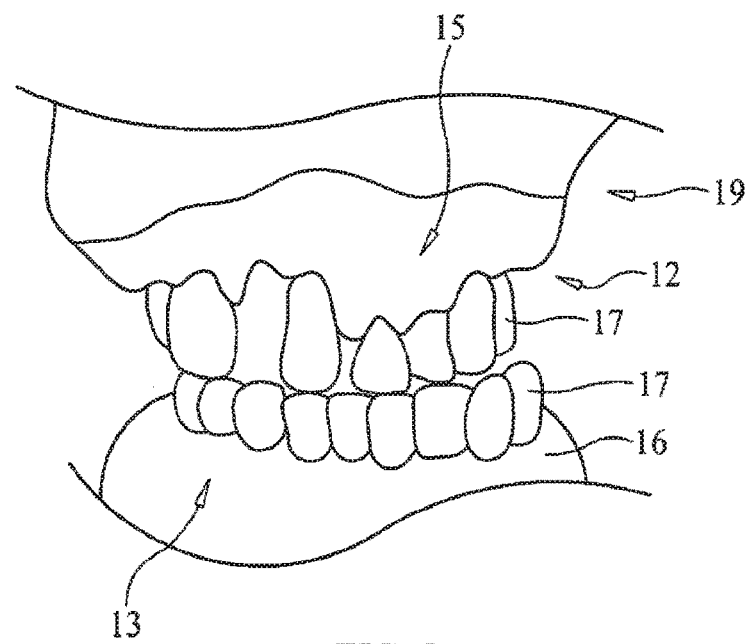
FIG. 8 is substantially an elevation view of patient's mouth showing exposed bone portion of the dental surgical site.
Figure 9:
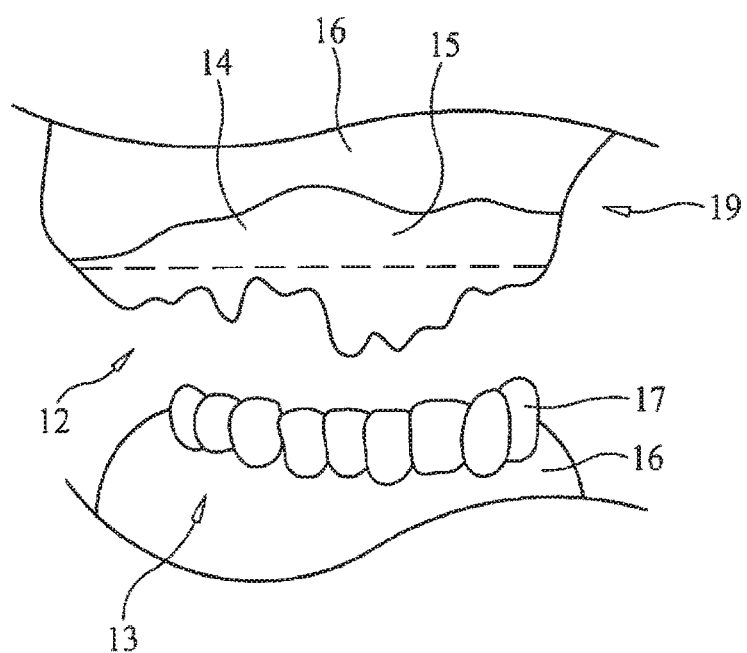
FIG. 9 is substantially an elevation view of patient's mouth showing exposed bone portion of the dental surgical site in an edentulous preoperative state.
Figure 10:
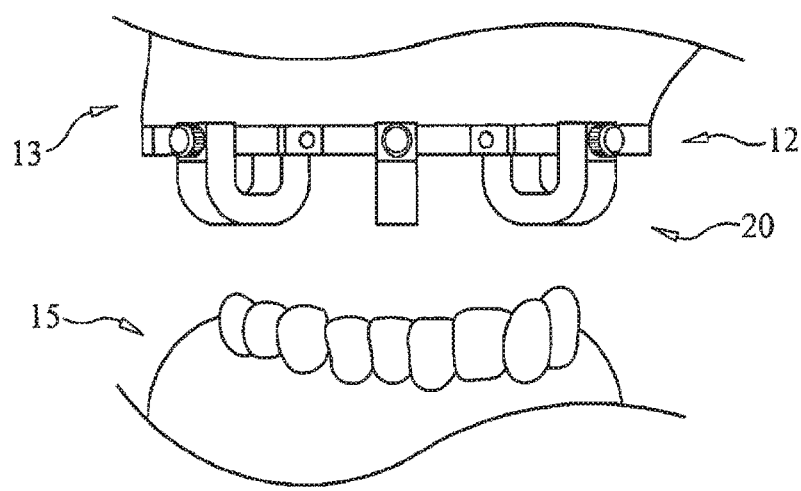
FIG. 10 is substantially a perspective front view of one embodiment of the bone foundation guide with struts being applied to the dental surgical site.
Figure 11:
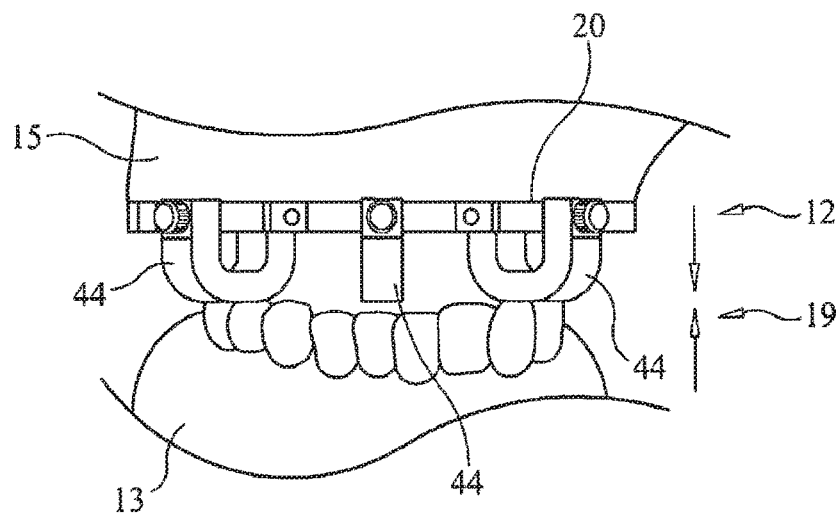
FIG. 11 is substantially a front perspective view of the bone foundation guide with struts being bitten down upon by the patient.
Figure 12:
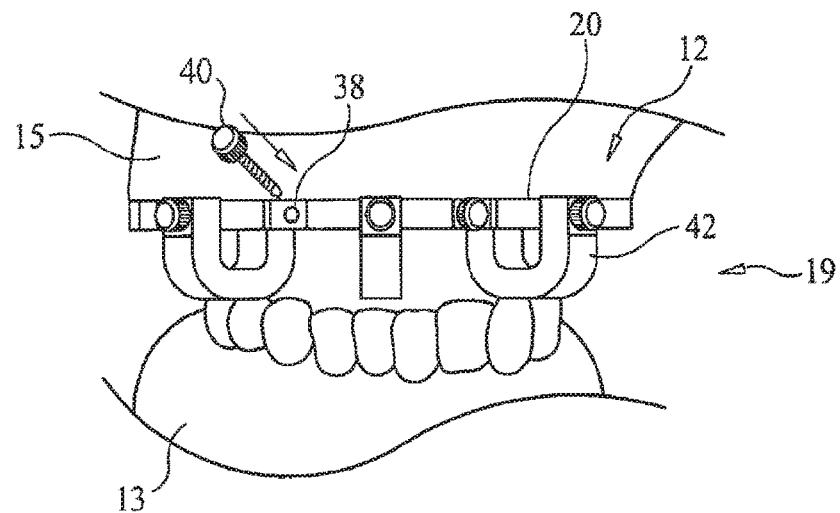
FIG. 12 is a front perspective view of the bone foundation guide with struts with the patient releasing its grip on the bone foundation guide and the strut fasteners being removed.
Figure 17:
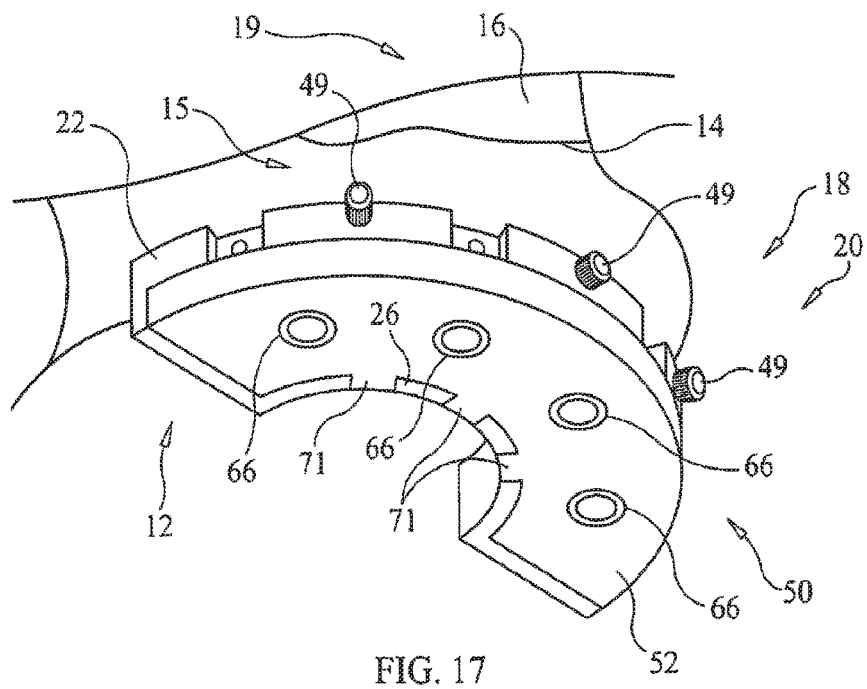
FIG. 17 is substantially an underside perspective view of the combination bone foundation guide and dental implant surgical guide combination.
Figure 18:
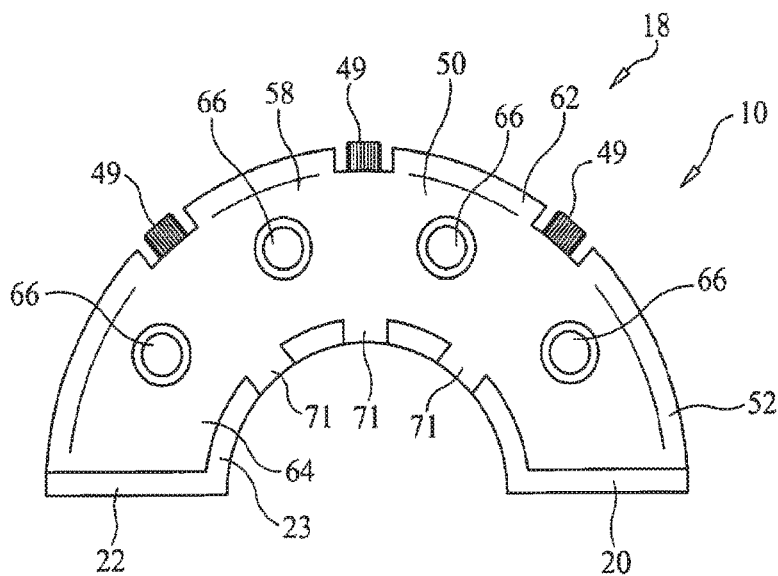
FIG. 18 is substantially an underside elevation view of the combination bone foundation guide and dental implant surgical guide combination.
Figure 19:
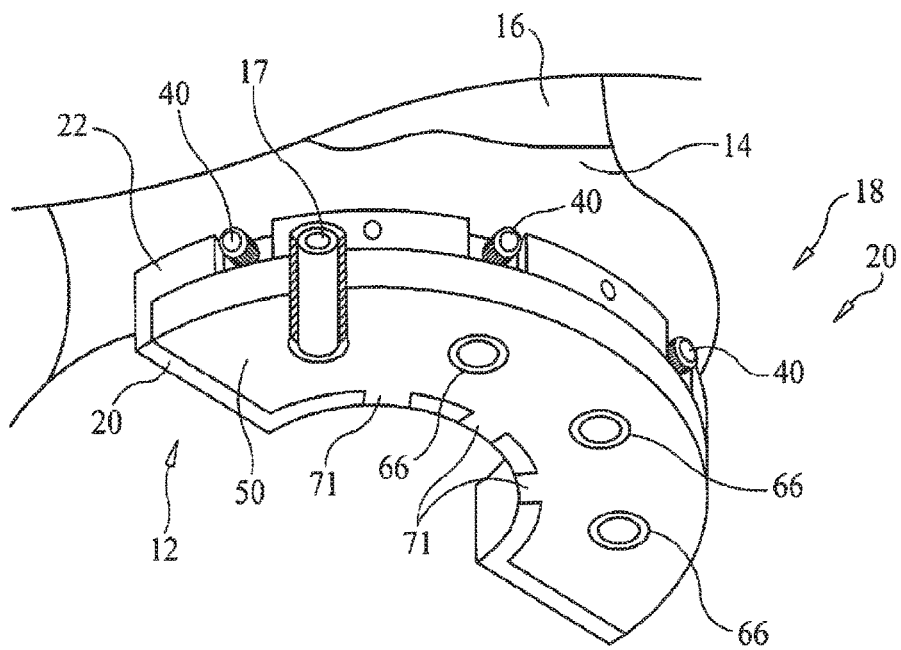
FIG. 19 is substantially a cutaway perspective view of the combination bone foundation guide and dental implant surgical guide combination.
Figure 20:
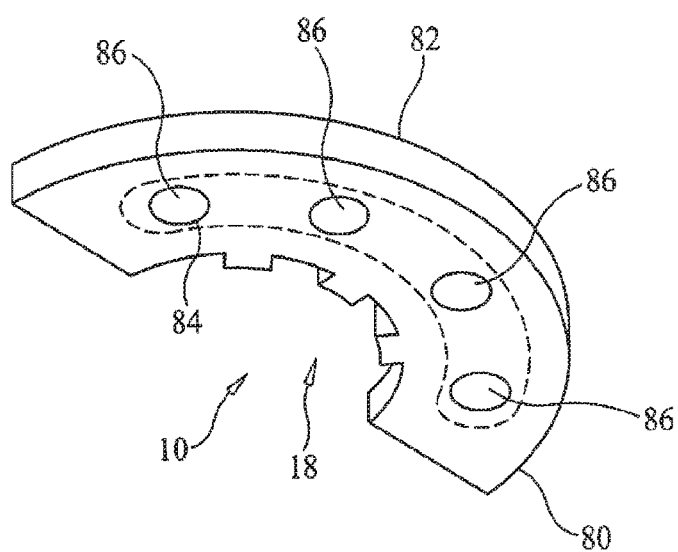
FIG. 20 is substantially a perspective view of the tissue spacer gasket.
Figure 21:
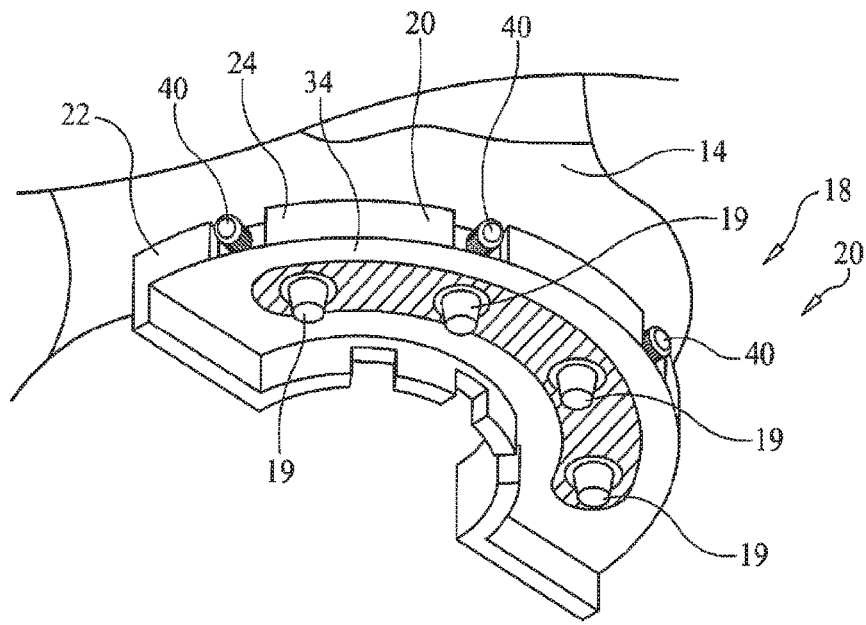
FIG. 21 is substantially a perspective view of the bone foundation guide with abutments attached to the implants.
Figure 22:
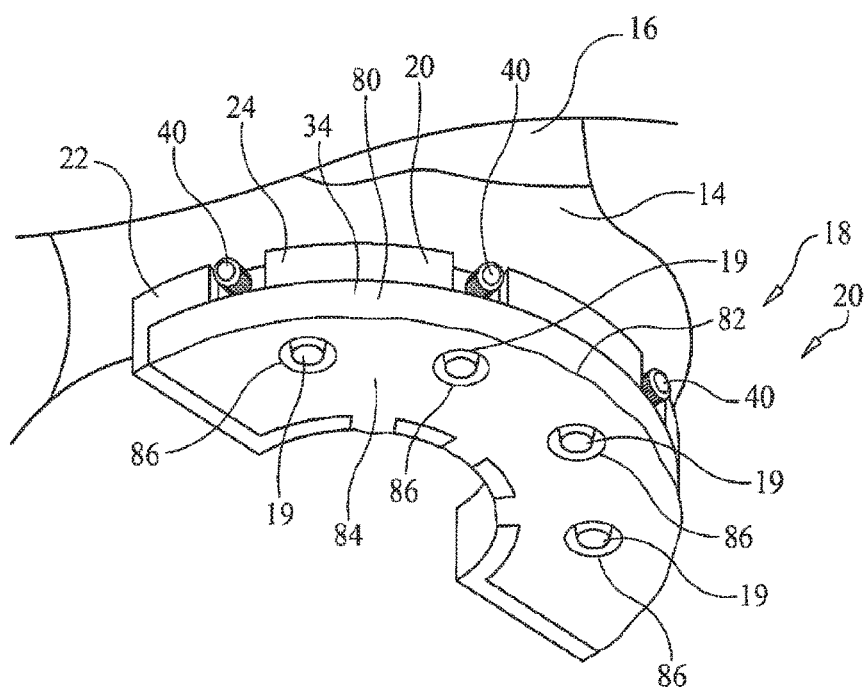
FIG. 22 is substantially a perspective view of the bone foundation guide and tissue gasket combination
Figure 23:
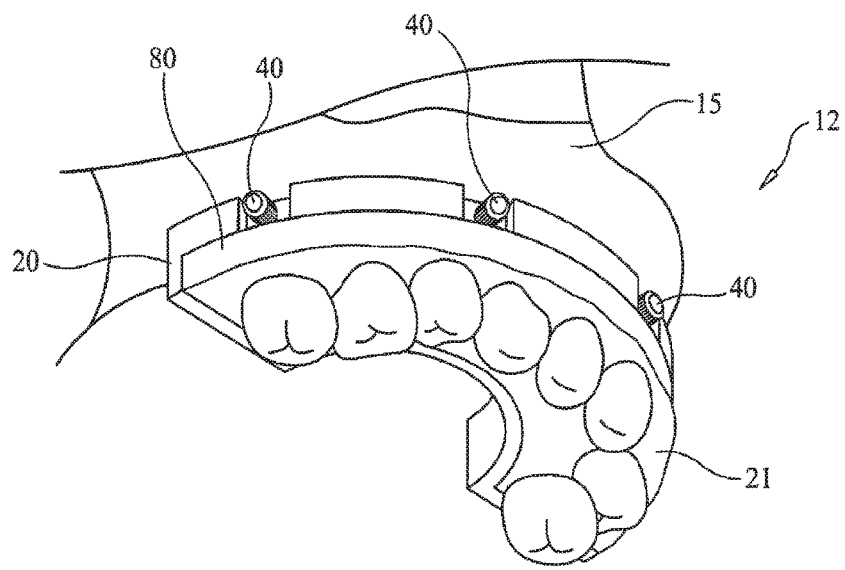
FIG. 23 is substantially a perspective view of the prosthesis applied to the bone foundation guide and tissue gasket combination.
Figure 24:
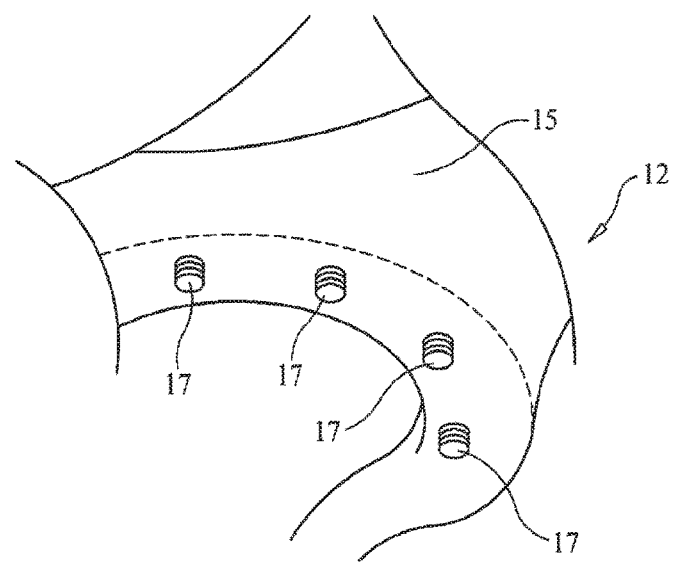
FIG. 24 is substantially a perspective view of the dental surgical site with the bone foundation guide, tissue gasket and prosthesis removed.
Figure 25:
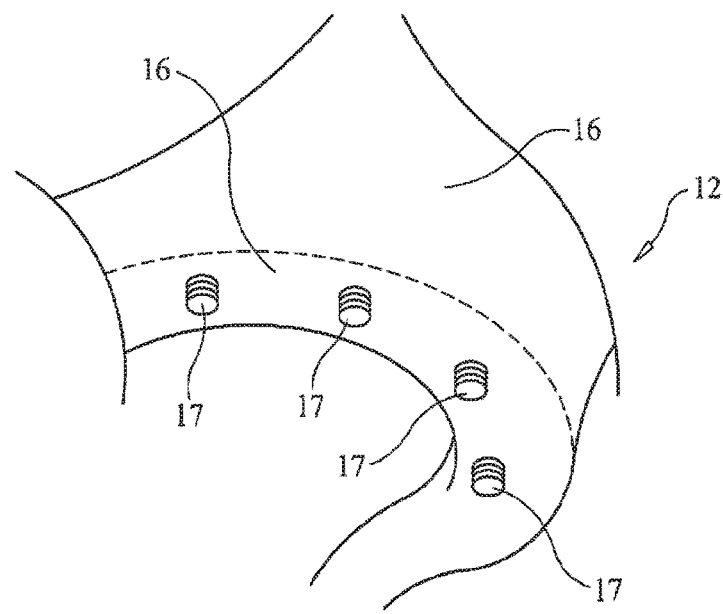
FIG. 25 is substantially a perspective view of the dental surgical site with the bone foundation guide, tissue gasket and prosthesis removed and gum tissue sutured back into place at the dental surgical site.
Figure 26:
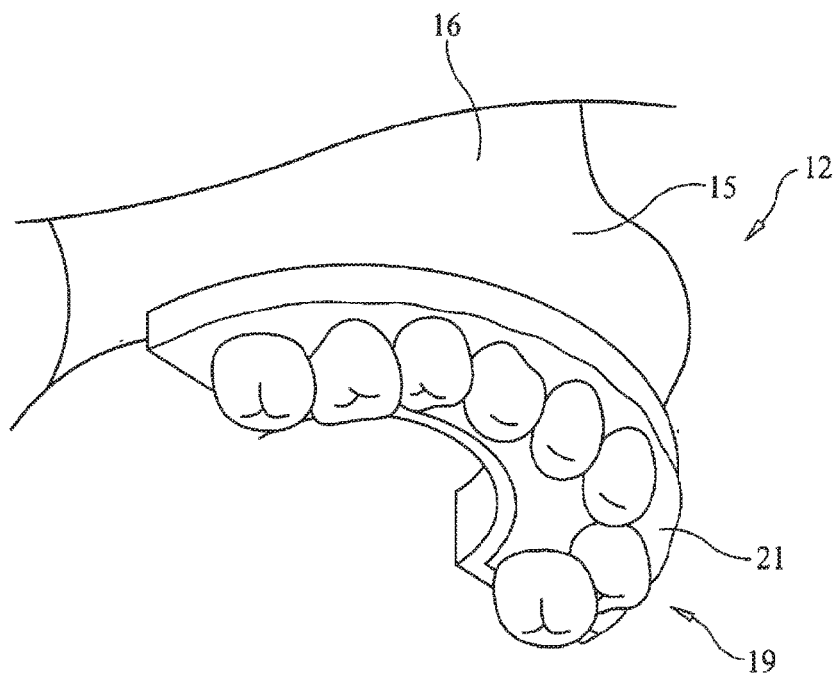
FIG. 26 is substantially a perspective view of the dental surgical site with gum tissue sutured back into place and prosthesis relocated upon the implants.

The present invention 10 could be a bone foundation guide system 18 and method or process 100. As substantially shown in FIGS. 1, 17, and 19 the bone foundation guide system 18 could comprise a bone foundation guide 20, a dental implant surgical guide 50 and in at least one embodiment, a tissue spacing gasket 80 as well. The bone foundation guide body 22, the dental implant surgical guide 50 and tissue spacing gasket 80 may be designed and created together through digital dentistry in which scans of the patients mouth 35 (along with impressions and castings thereof) may be used to create a virtual model (not shown) of the patient's existing mouth; to develop a virtual model of the patient's mouth both pre-dental and post-dental surgery; and to develop a dental surgical plan that connects the two patient-specific virtual models. In this manner, the dental surgical planning can provide for the manufacture the bone foundation guide 20, dental implant surgical guide 50 and tissue spacing gasket 80 so that the contours of the bone foundation guide body 22 may be created to fit upon the exposed bone 14 of the dental surgical site 12. Further, the dental implant surgical guide 50 contours may also match those of the dental implant surgical guide 50 and the tissue spacing gasket 80 to enable dental implant surgical guide 50 and the tissue spacing gasket 80 to alternately be removably attached to and be supported by the bone foundation guide 20.

As substantially shown in FIGS. 1, 2, 3, 4, 5 and 6 the bone foundation guide 20, as substantially used by a dental healthcare professional such as a dental surgeon (not shown) to substantially modify (e.g., reduce, augment or both) the bone 14 of the dental surgical site 12 as needed for a successful dental surgery. The bone foundation guide 20 could comprise a bone foundation guide body 22 with a buccal wall 24 and lingual wall 26 connected together at their respective ends by a first end 28 and a second end 30. The first end 28 and the second end 30 could be holding the buccal and lingual walls 24, 26 apart from one and other in a substantially parallel fashion to generally create and define an open surgical space 32 (e.g., that generally passes through the bone foundation guide body 22) to generally continuously connect a portion of the top 34 of the body 22 with a portion of the bottom 36 of the body 22.

Figure 13:
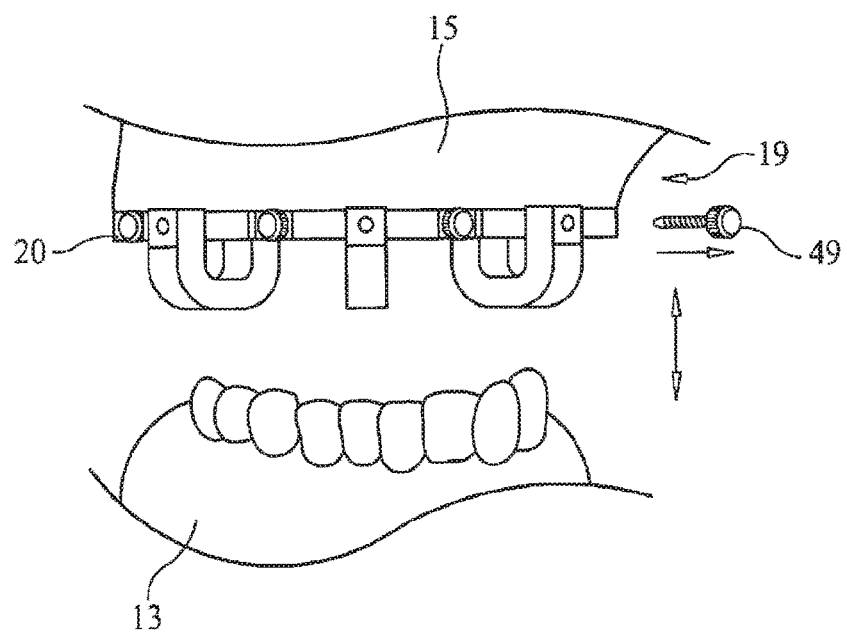
FIG. 13 is substantially a front perspective view of the bone foundation guide with struts, the strut fasteners being removed from the respective strut.
Figure 14:
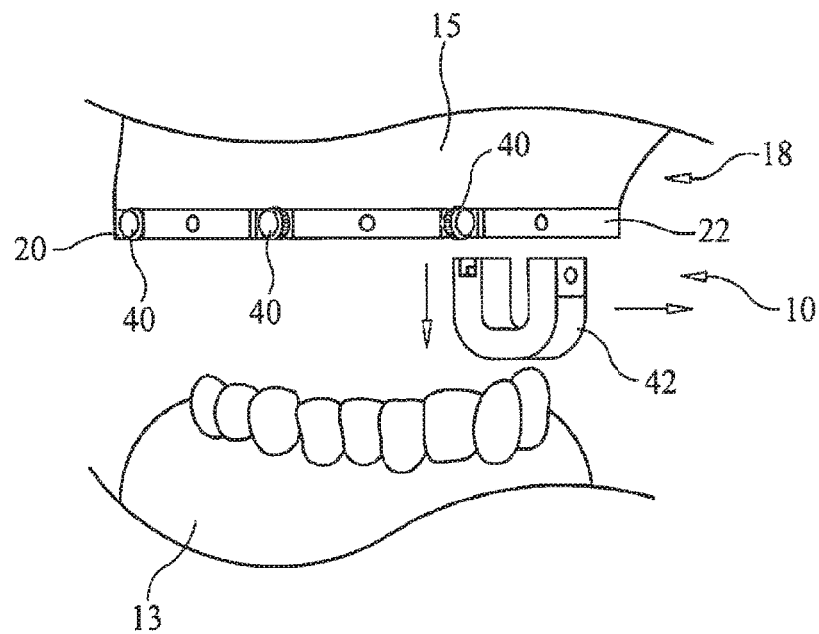
FIG. 14 is substantially a front perspective view of the bone foundation guide with struts, the strut being removed the bone foundation guide body.
Figure 15:
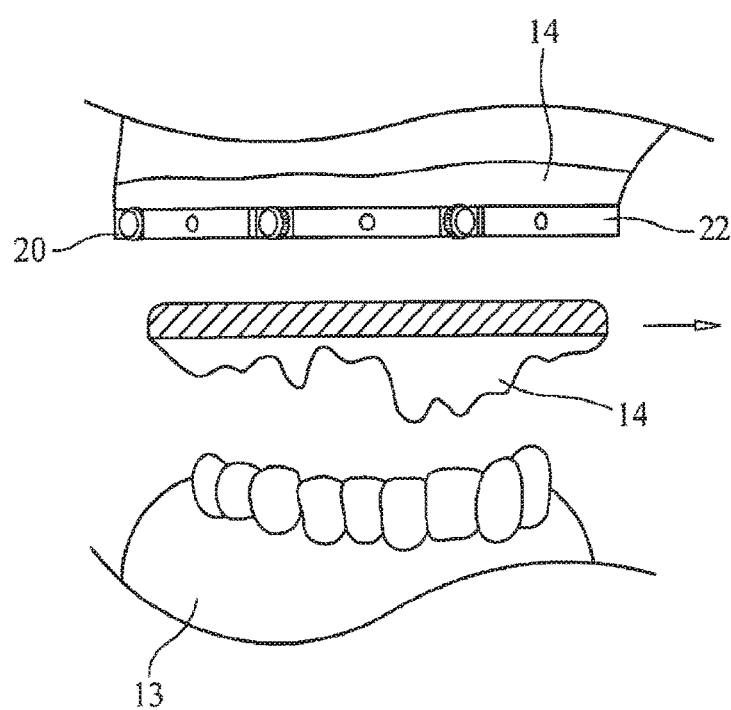
FIG. 15 is substantially a front perspective view of the bone foundation guide with struts removed and the harvested bone being removed from the dental surgical site.
Figure 15A:
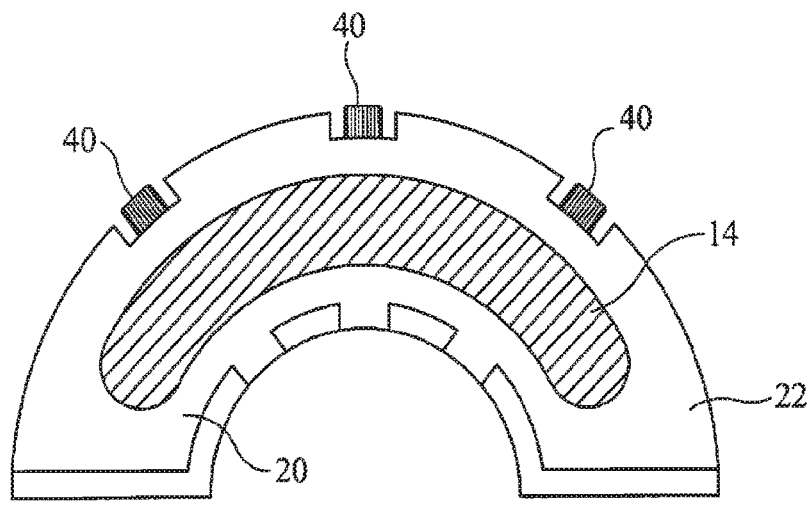
FIG. 15A is substantially a bottom elevation view of the bone foundation guide with struts and the harvested bone removed from the dental surgical site.
Figure 16:
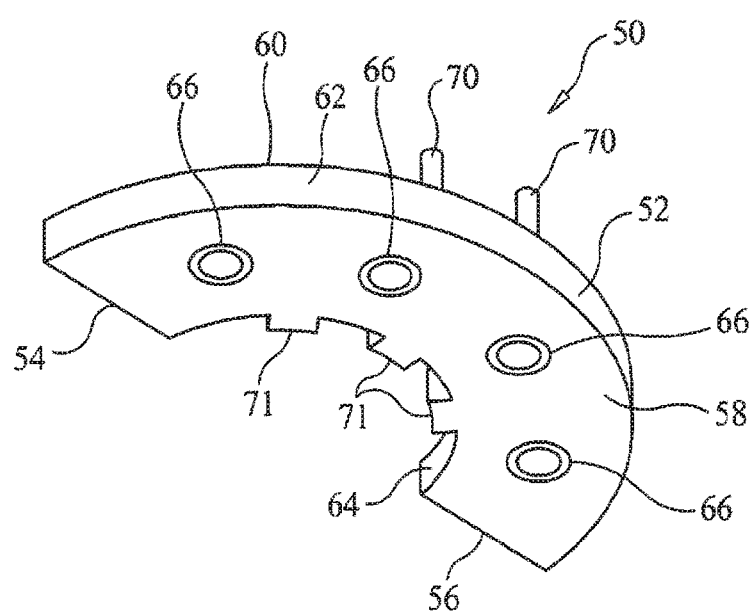
FIG. 16 is substantially an underside elevation view of the bone foundation guide with struts removed and the harvested bone removed from the dental surgical site

The bone foundation guide body 22 may be further penetrated by one or more attachment apertures 38 that may be oriented to pass through a buccal 24 wall. Body fasteners 40 may pass through the attachment apertures 38 to into the bone 14 of the dental surgical site 12 to removably secure the bone foundation guide body 22 to dental surgical site 12. (Substantially shown in FIG. 13.) The attachment aperture 38 could further feature a reinforcement collar (not shown) to support and guide the fastener 40 through the attachment aperture 38. In other embodiments, the attachment apertures 38 could pass though the body 22 connecting top 34 and bottom 36 or through the lingual wall 26 to provide body attachment to the dental surgical site 12. The body may further have a cutting guard 23 extending up from the top of the lingual wall 26 to prevent a cutting implement (not shown) when used with the bone foundation guide in removing bone 14 from a dental surgical site from unwantedly cutting the tongue or other portions of the patient's mouth 19. This cutting guard 23 may further feature out or more cutouts 25 that may be used to anchor and align other portions.

Some embodiments of the bone foundation guide body 22 may further comprise of a one or more anchoring struts 42 that may be removably attached to the buccal wall 24 and the lingual wall 26 between the first end 38 and the second end 30. The anchoring strut 42 may have at its outer apex 44 one or more indentations 46 that can match one or more portions of gum, dentition or both the patient's first or opposing alveolar ridge 28 (e.g., the opposing alveolar ridge 13 is located opposite of or opposing to the second alveolar ridge 15 that is supporting the dental surgical site 12. Meaning if the dental surgical site 12 is on the upper alveolar ridge then the opposing alveolar ridge 28 could be the lower alveolar ridge.) The front end 43 of anchoring struts 42 may be penetrated by strut apertures 47 that allow strut fasteners 49 (e.g., tapered pins) to penetrate through the anchoring strut 42 to the buccal wall 24. The strut fasteners 49 may removably attach to the anchoring strut 42 by the buccal wall 24 and be held in place by frictional force. The other or rear end 41 of the anchoring strut 42 may have a strut groove 48 that fits over a respective cutout 25. A tab 45 within the strut groove 48 may be removably received within the respective cutout 25 to further reversibly attach the rear end 41 to the cutting guard 23.

The anchoring strut 42 may allow the patient itself press at least a portion of gum tissue, dentition or both of the opposing alveolar ridge 13 upon at least one anchoring strut 42 of the bone foundation guide 21 to generally hold the bone foundation guide 21 in place upon the dental surgical site 12 (e.g., the exposed bone) in particular, that portion of gum tissue, dentition or both of the opposing alveolar ridge 13 could be received with the indentation(s) 46. The patient's action (e.g., substantially clamping down with patient's mouth upon the bone foundation guide 20 in situ could allow the patient to temporarily and removably hold the bone foundation dental upon the dental surgical site while the dental health care professional (not shown) is free to use both hands to attach the bone foundation guide 21 in place with body fasteners. Once the bone foundation guide 21 is secured by body fasteners 40 to the bone portion of the dental implant surgical site 12, the patient could remove one or more portions of the opposing alveolar ridge 28 from the one or more indentations 46 upon the one or more anchoring struts 42 (e.g., the patient opens its mouth to stop biting upon the anchoring struts 42.) The dental health care professional can then proceed with the removal of the strut fasteners 49 from the bone foundation guide 21 so as to be able to lift the anchoring struts 42 free and clear from the body 22.

The use of anchoring struts 42 can also be applied to bone reduction guides that lack the present inventions ability to combine or stack together with the dental implant surgical guide or tissue spacing gasket. In such instances, bone reduction guides are not contoured to accept the dental implant surgical guide or tissue spacing gasket but could have a body to which the anchoring struts 42 are applied to allow the patient to substantially clamping down with patient's mouth upon the bone reduction guide in situ could allow the patient to temporarily and removably hold the bone reduction guide upon the dental surgical site. The portions of dentition, teeth or both of the opposing alveolar ridge could be received with the impressions located upon the apex of anchoring struts 42 to hold the bone reduction guide in place while the dental health care professional (not shown) is free to use both hands to attach the bone reduction guide in place with fasteners to the dental surgical site. Once the fasteners have secure the bone reduction guide to the dental surgical site, the patient could release its bite upon the anchoring struts. The dental healthcare professional can then remove the anchoring struts 42 from the body of the bone reduction guide to allow the bone reduction guide to be used to alter bone structure at the dental surgical site.

As substantially shown in FIGS. 16, 17, 18, and 19 once the anchoring strut(s) 42 are removed from the bone foundation guide body 22, the dental implant surgical guide 50 could be removably attached to the top 34 of the body 22. The dental implant surgical guide 50 could be so anchored to dental surgical site 12 to generally allow dental implant surgical guide 50 to be substantially be used to guide and locate the placement of dental implants within dental surgical site 12.

The dental implant surgical guide 50 could comprise a dental surgical guide body 20 having a first end side 52 and second end side 54 that terminates the dental surgical guide body 52 and along with a top side 58 and a bottom side 60 that continuously connect a buccal side 62 with a lingual side 64. The bottom side 60 of the dental implant surgical guide 50 can be digitally designed and manufactured to have a contour that substantially matches and removably accepts the top 34 of the bone foundation guide 20. The top 34 of the bone foundation guide body 22 may also be digitally designed and created to substantially match and to receive the bottom side 60 of the reciprocal dental surgical guide body 52 to allow the conjoining of the two guides 20, 50 in a stackable manner so that the bone foundation guide 20 acts as a base or foundation for the dental implant surgical guide 50.

The dental surgical guide body 52 can be further penetrated by one or more implant apertures 66 that could continuously connect the top side 58 to the bottom side 60 to guide implant preparation and attachment to the dental operation site 12. The dental surgical guide body 52 to removably attach to the body 22 could utilize a wide variety of attachment means. One such possible attachment means could make use one or more guide pins 70 and one or more guide tabs 71 and their frictional interplay with the body 22. The guide pins 70 could protrude out from the bottom side 60 by the buccal wall 62 to be removably received within pin apertures on the top 34 of the body 22 along the buccal wall 24. The one or more guide tabs 71 could extend outwards from the lingual side 64 to be respectively received by the cutouts 25 of the cutting guard 23. The guide tabs 71 and guide pins 70 along with the lingual side 64 matching the contour of the cutting guard 23 could provide a snap-in fit of the dental implant surgical guide 50 to the bone foundation guide 20.

The conjoining or stacking capability of the two guides 20, 50 could alleviate the need to remove the bone foundation guide 20 from the dental surgical site 12 prior to attaching the dental implant surgical guide 50 to the dental surgical site 12 as well as alleviate the need to attach the dental implant surgical guide 50 directly to the dental surgical site 12 and the like. This combining of the two guides 20, 50 could also reduce the time, money, effort, patient discomfort and alike that would otherwise occur if the guides 20, 50 were used separately from one and other. When so combined together, the dental implant surgical guide 50 generally surrounds the bone foundation guide's open surgical space 32 to allow implant components, implants or both to pass through the dental implant surgical guide's implant aperture(s) 66 and on through the of the open surgical space 32.

As substantially shown in FIGS. 20, 21, 22 and 23, one other possible embodiment of the invention 10 could further comprise a tissue spacing gasket 80 that can be alternatively used with the bone foundation guide 50 instead of the dental implant surgical guide 50 or the anchoring strut(s) 42. The tissue spacing gasket 80 could fit between the bottom 36 of the bone foundation guide 20 and the dental surgical site 12 to allow the proper placement of prosthesis 21 upon the placed implants by providing an approximation of the distance or thickness of the gum tissue 16 that otherwise covers the dental surgical site 12. The placement of the tissue spacing gasket 80 upon the bone foundation guide top 34 where the tissue spacing gasket 80 is generally sandwiched between the bone foundation guide 20 and the prosthesis 21 could allow the tissue spacing gasket 80 provide additional benefits besides correcting for thickness of the missing (e.g., peeled back) gum tissue 16. The tissue spacer guide 80 could help cradle the prosthesis and maintain the prosthesis proper vertical and centric positions as the prosthesis is being fixed upon the implants. When the prosthesis 21 is generally fixed about the implants (e.g., to the abutments 17 attached to the implants), dental acrylic could be injected into the prosthesis to secure implant abutments to the prosthesis. The tissue spacing gasket 80 could help block out the undercut of the abutments 17 to generally prevent the acrylic from reaching the undercuts and thus preventing unwanted or premature attachment of the prosthesis to the implants 17. The tissue spacing gasket 80 could further prevent acrylic from reaching and contaminating the exposed bone 14.

The tissue spacing gasket 80 could be made from a pliable polymer that forms a gasket top 84 upon which the prosthesis could rest and to a gasket bottom 82 which is reversibly received by the bone foundation top 34, the gasket top 84 and the gasket bottom 84 being continually connected by one or more gasket apertures 86. The one or more gasket apertures 86 could have the same alignment and size of the implant apertures 66 of the dental implant surgical guide 50. In at least one embodiment, the tissue spacing gasket 80 could denote a gasket open surgical space (not shown) that continuously connects gasket top 84 and gasket bottom 82, the gasket open surgical space generally matching the footprint of the bone foundation guide's open surgical space 32.

To generally removably affix the tissue spacing gasket 80 to the bone foundation guide 20, the tissue spacing gasket 80 could have one or more gasket pins that protrude from the gasket bottom 82 and could be removably received within apertures on the bone foundation guide top 34 by the buccal wall 24 that received guide pins 70. The tissue spacing gasket 80 could further have the gasket tabs 88 that could be removably be received within the cutting guard cutouts 25. The tissue spacing gasket tabs 88 could generally match the size, placement and orientation of the dental implant surgical guide's guide tabs 71

As substantially shown in FIGS. 7-25, one possible method or process 100 for the use of the invention could start with step 102, digital scanning and modeling for the patient-specific dental surgery. In this step, dental digital methods (digital dentistry) may be used in creating patient-specific map of the patient's mouth (which could include the digital scanning of analogue appliances such as patient specific castings and impressions); in creating models for patient-specific bone remodeling (e.g., foundation and re-contouring) of the upper and/or lower dental struts in the patient's mouth; in creating models for dental implant surgical guides/bone foundation guides and prosthetics used post-patient-specific bone remodeling; in creating a patient specific model of the patient's mouth post dental surgery. After this step is substantially completed, the process 100 could proceed to step 104, creation of the guides, tissue spacing gasket and other dental appliances.

In step 104, creation of the guides and other dental appliances, the acquired and processed modeling data can be used to create the patient-specific bone foundation guide (e.g., d patient-specific bone foundation guide, tissue spacing gasket and dental implant surgical guide that be stacked together in various combinations. The anchoring struts can also be patient-specific made to have indentations at their respective apexes to match various portions of the dentition, tissue or both of the opposing alveolar ridge. Once manufactured, the anchoring struts could be removably attached to the bone foundation body. The strut fastener (e.g., a tapered pin) could removably attach the anchoring strut's front end to the buccal wall. The strut rear end could removably straddle the cutting guard's respective cutout with the strut groove allowing the strut groove's tab to be removably received within the cutout.

The design and manufacturing imparted stacking capability could allow the two guides and gasket to come together to various stacked combinations. This stacking capability allows the bone foundation guide, once removably secured to the dental surgical site by the dental health care profession, to generally act as foundation for the dental implant surgical guide or the spacing tissue gasket to secure them alternately to the dental surgical site. This stacking capability could allow the implant, implant components, implant instruments and the like to be guided through the dental implant surgical guide implant apertures and the bone foundation guide's open surgical space to properly interact with the dental surgical site. After this step is substantially completed, the process 100 could proceed to step 106, surgical prep.

In step 106, surgical prep, the dental health care professional could (after properly anesthetizes the patient and instituting other required dental surgical pre-operation protocols) could make incisions in the gum area of the dental surgical site, and peel back the gum tissue to expose the portion of bone being operated upon at the dental surgical site. Any teeth at the dental implant surgical site can be removed. If the patient's dental health has declined enough, the alveolar ridge supporting the dental surgical site could be made edentulous After this step is substantially completed, the process 100 could proceed to step 108, use of the bone foundation guide.

In step 108, use of the bone foundation guide, the bone foundation guide is initially placed upon to the dental surgical site (e.g., the open surgical space being contoured to generally match and receive segment of the exposed bone.) The dental healthcare professional than asks the patient to "bite" down upon or "bite" up against) the bone foundation guide (e.g., using the portion of the dentition, tissue or both of the opposing alveolar ridge) to substantially hold the bone foundation guide initially in place upon the dental surgical site. As the portion of the dentition, tissue or both of the opposing alveolar ridge comes in contact with the anchoring strut(s) the portion may be received within the one or more indentations on the apex(s) of the anchoring strut(s).

The dental healthcare professional with both hands free can then use a drill to make channels in the dental surgical site (e.g., the exposed bone portion) utilizing the attachment apertures. Body fasteners are placed into the attachment apertures and channels to generally removably attach the bone foundation guide to the exposed bone at the dental surgical site. The dental healthcare professional asks the patient to relax its grip upon the bone foundation guide to generally bring the portion of the dentition, tissue or both of the opposing alveolar ridge out of contact with the indentation(s). As the anchoring struts are cleared so cleared, the strut fastener(s) can be removed along with the anchoring strut(s) from the bone foundation guide.

The removal of the anchoring struts from the bone foundation guide's top, clears top so the top can be used to guide a cutting implement (e.g., blade saw) to reduce the dental surgical site's bone structure. The harvested bone (or bone analogue) could then be used to augment the dental surgical site if needed. Known dental techniques for reducing or augmenting the bone could be employed to provide the proper bone contour for the dental surgical site. Once this step is substantially completed, the process 100 could proceed to step 110, use of the dental implant surgical guide.

In step 110, use of the dental implant surgical guide, the dental health care professional could place the bottom side of the dental implant surgical guide upon the top of the bone foundation guide generally enclosing the open surgical space. In one embodiment, the tissue spacing gasket is sandwiched between the bone foundation guide and the dental implant surgical guide. Pins on the underside of the dental implant surgical guide could attach to the attachment apertures in the bone foundation guide top (e.g., by the buccal wall) while the guide tabs extending out from the lingual side could removably engage the cutting guard cutouts to provide a snap fit of the dental implant surgical guide into the bone foundation guide.

The dental healthcare professional could use the bone foundation guide and the dental implant surgical guide stacked or otherwise combined together to substantially direct and operate implant preparation implements (e.g., drills, reamers, and the like), implant components, or both by passing them through the dental implant surgical guide and into the open surgical space to properly prepare the dental surgical site to receive the implant(s) This implant preparation could ensure there was proper orientation and telemetry of the implant components and implants into the generally exposed bone of the dental surgical site. Once the bone is properly prepared to receive the implants, the implant(s) could then pass through the combination to be anchored into the bone. Once this step is substantially completed, the process 100 could proceed to step 112, using tissue spacing gasket.

In step 112, using tissue spacing gasket, once the implants were properly located and set within the dental surgical site, the surgical implant dental guide could be removed from the bone foundation guide and the tissue spacer gasket could alternatively be connected to the bone foundation guide. In one embodiment, the pins located on the gasket bottom can be generally be removably received in the same apertures on the bone foundation guide top that the accommodated the guide pins of the dental implant surgical guide.

In one possible embodiment, once the tissue spacing gasket is removably attached to the bone foundation guide then temporary abutments can be placed upon the implants. A temporary prosthesis can be placed over the tissue spacer gasket to come into contact the temporary abutments. The tissue spacing gasket could cradle the temporary prosthesis at this point holding it in the proper vertical and concentric orientation as dental acrylic is injected into the temporary prosthesis to secure the abutments to the temporary prosthesis. The tissue spacing gasket may further prevent the acrylic from leaking upon and contaminating the exposed bone. The tissue spacing gasket may as well as prevent any acrylic leaking onto the abutment undercut (e.g., to generally prevented unwanted premature attachment of the prosthesis to the implants.) The tissue spacing gasket may help to insure that proper distance between bone and prosthesis is maintained to account for presence of tissue when the gum tissue is placed back over the bone.

Once the acrylic has set, the above abutment prosthesis attachment process may repeated used for a clear or analogue prosthesis that later can be sent back to the lab. The analogue prosthesis with its affixed abutments may be applied to implant bone model that was devised through the dental model to see how the dental healthcare professional may have deviated from the original dental surgical plan in attaching the implants to the dental surgical site. In that manner, the analogue prosthesis will allow the final changes of the actual dental surgery (on site changes made by the dental healthcare professional to take into account issues not foreseen by the dental surgical plan) to be imparted onto the dental model and to the final prosthesis.

Once the temporary prosthesis (and analogue prosthesis) is removed from the tissue spacing gasket-bone foundation guide combination, the tissue spacing gasket could be removed from the bone foundation guide. The gum tissue flaps could be sutured back over the exposed bone (but not necessarily over the implants) and the temporary prosthesis could be reattached to the implants. As the dental surgical site heals and the implants further incorporate themselves into the bone structure, the temporary prosthesis could help maintain the implant positioning as set during the surgery, so that the permanent prosthesis should be able to replace the temporary prosthesis with minimal adjustment and fitting.

This process 100 could also allow as needed, use of temporary cylinder, associated seals, additional filling, and other sealing methods that may be used to properly prepare the dental implant for the attachment of prosthesis and the like. If healing abutments are used instead, then they can be fitted to the implants as needed. The gum tissues can then be sutured or otherwise cover-up the exposed bone to meet up with the abutment/implants. If the gum tissues need to heal or need to heal around the healing abutments or the implants require ossification to secure them in place to the bone, then after these event(s) have occurred/or a suitable amount of healing time has passed then the final prosthesis (or prosthetic) could be placed upon the implants in a secure fashion. After this step is substantially completed, the process 100 could proceed back to step 102 as needed.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As shown in the specification, drawings, claims and abstract, the invention, a bone foundation guide provides for the combining or stacking together as one unit, a bone foundation guide, a dental implant surgical guide and tissue spacing gasket. The use of removable anchoring struts allows the patient to apply the opposing alveolar ridge to the apex of the one or more removable anchoring struts to initially hold the bone foundation guide in place upon the dental surgical site. The action frees the dental healthcare professional to use both hands to more securely attach the bone foundation guide to the dental implant site with fasteners. The patient can remove opposing alveolar ridge from the anchoring struts to allow the anchoring struts to be removed from bone foundation guide to expose the top for bone reduction actions (or bone augmentation actions.) The strut removal allows the tissue spacing gasket and dental implant surgical guide to be alternatively used with the bone foundation guide in generally securely stacked manner for use upon the dental surgical site for the placement and attachment of one or more dental implants at the dental surgical site.

What is claimed is:

1. A bone foundation guide system comprising:
  A) a bone foundation guide comprising a body having a buccal wall and a lingual wall that is continuously connected by a first end and a second end forming an open surgical space connecting a top of the body with a bottom of the body, wherein the bottom is contoured to reversibly affix the body to at least a portion of a bone segment of a dental implant surgical site while the top is contoured to match a bottom side of a dental implant surgical guide as well as to guide the removal, augmentation or both of the bone segment from a dental surgical site; and
  B) one or more anchoring struts, wherein at least one of the one or more anchoring struts is configured to removably attach to the body to connect the buccal wall to the lingual wall, an apex of the at least one of the one or more anchoring struts further denoting one or more indentations for matching up with and receiving one or more portions of a gum tissue, dentition or both of an alveolar ridge that opposes the dental surgical site.

2. The bone foundation guide system of claim 1 wherein the one or more indentations are configured such that the reception of one or more portions of a gum tissue, dentition or both of the opposing alveolar ridge into the one or more indentations locates the body of the bone foundation guide onto the portion of the bone segment.

3. The bone foundation guide system of claim 2 further comprising fasteners to be received within the bone segment to thereby secure the body of the bone foundation guide onto the dental surgical site.

4. The bone foundation guide system of claim 1 further comprising one or more strut fasteners that are configured to pass through the one of the one or more anchoring struts to removably attach the one of the one or more anchoring struts to the body of the bone foundation guide.

5. The bone foundation guide system of claim 4 wherein one of one or more strut fasteners is configured to connect the one of the one or more anchoring struts to the buccal wall while a portion of the one of the one or more anchoring struts fits into a channel of the lingual wall.

6. A bone foundation guide comprising:
A) a body having a buccal wall and a lingual wall that is continuously connected by a first end and a second end forming an open surgical space connecting a top of the body with a bottom of the body, wherein the bottom is contoured to reversibly affix to at least a portion of a bone segment of a dental implant surgical site while the top is contoured to guide at least an alteration of the bone segment; and
B) at least one anchoring strut that is configured to removably attach to the body and span across the top of the body to connect the buccal wall to the lingual wall, the at least one anchoring strut having an apex further denoting one or more indentations having at least one contour that is configured and positionable to match one or more portions of one alveolar ridge opposite another alveolar ridge that supports the dental implant site.

7. The bone foundation guide of claim 6 wherein the one or more indentations are configured such that the reception of the one or more portions of the opposing alveolar ridge into the one or more indentations initially secures the body of the bone foundation guide onto the bone segment.

8. The bone foundation guide of claim 6 further comprising one or more fasteners that are configured to pass through the body of the bone foundation guide and be received within the bone segment to thereby additionally secure the body of the bone foundation guide onto the dental surgical site.

9. The bone foundation guide of claim 6 wherein the one or more anchoring struts are configured such that removal of the one or more anchoring struts allows access to the top that is contoured to guide at least an alteration of the bone segment.

10. A method of holding a bone foundation guide to a dental surgical site, wherein the dental surgical site is supported by a first alveolar ridge, the method comprising the following steps:

(A) providing a bone foundation guide comprising a body having a buccal wall and a lingual wall that is continuously connected by a first end and a second end forming an open surgical space that further connects a top of the body with a bottom of the body, wherein the bottom is further contoured to removably receive at least a portion of a bone segment of a dental implant surgical site while the top is contoured to reversibly receive a dental implant surgical guide as well as guide a modification of an exposed bone of the dental surgical site;

(B) providing at least one anchoring strut, wherein the at least one anchoring strut has an apex denoting one or more indentations for receiving one or more portions of tissue, dentition, or both of a second alveolar ridge that is opposing the first alveolar ridge supporting the dental surgical site;

(C) removably attaching the at least one anchoring strut to the body;

(D) holding the bone foundation guide in place upon the dental surgical site by bringing the one or more portions of tissue, dentition, or both of the second alveolar ridge into contact with the at least one of the one or more anchoring struts.

11. The method of claim 10 further comprising the step of removing one or more portions of tissue, dentition, or both of the second alveolar ridge from contact with the one or more anchoring struts to allow removal of the one or more anchoring struts from the body of the bone foundation guide.

12. The method of claim 11 further comprising a step of temporarily locating either the dental implant surgical guide or a tissue spacing gasket upon the bone foundation guide after removing the one or more anchoring struts form the body of the bone foundation guide.

* * * * *